United States Patent
De Luigi

(10) Patent No.: US 11,154,465 B2
(45) Date of Patent: Oct. 26, 2021

(54) COSMETIC COMPOSITIONS IN FORMS OF AQUEOUS GELS AND USES THEREOF

(71) Applicant: B. KOLORMAKEUP & SKINCARE S.P.A., Treviglio (IT)

(72) Inventor: Mario De Luigi, Milan (IT)

(73) Assignee: B. KOLORMAKEUP & SKINCARE S.P.A., Treviglio (IT)

(*) Notice: Subject to any disclaimer, the term of this patent is extended or adjusted under 35 U.S.C. 154(b) by 154 days.

(21) Appl. No.: 16/310,408

(22) PCT Filed: Jul. 6, 2017

(86) PCT No.: PCT/IB2017/054078
§ 371 (c)(1),
(2) Date: Dec. 14, 2018

(87) PCT Pub. No.: WO2018/007974
PCT Pub. Date: Jan. 11, 2018

(65) Prior Publication Data
US 2019/0328628 A1 Oct. 31, 2019

(30) Foreign Application Priority Data
Jul. 6, 2016 (IT) .................. 102016000070453

(51) Int. Cl.
| | |
|---|---|
| A61Q 1/10 | (2006.01) |
| A61K 8/04 | (2006.01) |
| A45D 40/26 | (2006.01) |
| A61K 8/19 | (2006.01) |
| A61K 8/34 | (2006.01) |
| A61K 8/55 | (2006.01) |
| A61K 8/73 | (2006.01) |
| A61K 8/81 | (2006.01) |

(52) U.S. Cl.
CPC .............. *A61K 8/042* (2013.01); *A45D 40/26* (2013.01); *A61K 8/19* (2013.01); *A61K 8/34* (2013.01); *A61K 8/345* (2013.01); *A61K 8/347* (2013.01); *A61K 8/55* (2013.01); *A61K 8/73* (2013.01); *A61K 8/8147* (2013.01); *A61Q 1/10* (2013.01); *A45D 2200/1072* (2013.01); *A61K 2800/43* (2013.01); *A61K 2800/48* (2013.01); *A61K 2800/87* (2013.01)

(58) Field of Classification Search
None
See application file for complete search history.

(56) References Cited

U.S. PATENT DOCUMENTS

| | | |
|---|---|---|
| 4,850,727 A | 7/1989 | Gueret |
| 4,974,980 A | 12/1990 | Gueret |
| 5,219,560 A | 6/1993 | Suzuki et al. |
| 2005/0276771 A1 | 12/2005 | Farsedakis et al. |
| 2015/0056153 A1* | 2/2015 | Allen ............. A61K 8/8147 424/70.7 |
| 2015/0265504 A1 | 9/2015 | Crane et al. |
| 2016/0136060 A1 | 5/2016 | Crane et al. |

FOREIGN PATENT DOCUMENTS

| | | |
|---|---|---|
| CN | 104352359 A | 2/2015 |
| EP | 1025832 A1 | 8/2000 |
| JP | 2016041676 A | 3/2016 |

OTHER PUBLICATIONS

Unknown, "DAITOSOL 5000AD" Daito Kasei, Oct. 2014, 2 pages.
Unknown, "Line Define Matte Peel-Off Eyeliner", Mintel, Jul. 2014, 3 pages.
Unknown, "Bright Eye Duo Liquid Eyeliner", Mintel, Jan. 2015, 3 pages.
Unknown, "Formulation Concept & Formula", Daito Kasei, In-Cosmetics Asia 2015, 48 pages.
Unknown, "The world of colors in cosmetics", CosmEthics, Jan. 7, 2015, 8 pages.
Unknown, "Surfactant", CosmeticOBS-L'Observatoire des Cosmétiques, Dec. 30, 2009, 3 pages.
Communication pursuant to Rule 114(2) EPC regarding Third Party Observations in corresponding International Application No. 17748572.9 dated Aug. 29, 2019, 6 pages.
International Search Report and Written Opinion dated Sep. 12, 2017, in corresponding PCT Application No. PCT/IB2017/054078, 15 pages.
Office Action dated Dec. 28, 2020, in corresponding Chinese Application No. CN 201780038088.8, with English-language Summary, 8 pages.

* cited by examiner

*Primary Examiner* — Jyothsna A Venkat
(74) *Attorney, Agent, or Firm* — MH2 Technology Law Group, LLP

(57) ABSTRACT

A cosmetic composition in a form of an aqueous gel may include (percentages by weight referred to weight of the cosmetic composition): greater than or equal to 5% and less than or equal to 30% of at least one inorganic pigment; greater than or equal to 10% and less than or equal to 50% of at least one film-forming agent including at least one acrylic copolymer comprising two or more monomers selected from: acrylic acid, methacrylic acid, $C_1$-$C_8$ alkyl acrylate, or $C_1$-$C_8$ alkyl methacrylate; greater than or equal to 0.05% and less than or equal to 3% of at least one thickening agent; greater than or equal to 0.1% and less than or equal to 5% of at least one surfactant; greater than or equal to 1% and less than or equal to 20% of at least one $C_1$-$C_4$ alkanol; and water equal to the complement to 100%.

20 Claims, No Drawings

COSMETIC COMPOSITIONS IN FORMS OF AQUEOUS GELS AND USES THEREOF

The present invention relates to a cosmetic composition in form of aqueous gel, particularly suitable for use as eyeliner to decorate the contour of the eyes. In particular, the cosmetic composition according to the present invention is suitable for use as a peelable eyeliner, i.e. an eyeliner removable from the application surface by peeling.

In the field of cosmetics, the need for cosmetic compositions in the form of aqueous gel is particularly felt. Aqueous gels are in fact applied more easily than liquid compositions, in particular in the eye area, and cause less dehydration of the skin. Aqueous-based compositions, moreover, are in general easier to remove and occlude the skin pores less.

Eye cosmetic products are known in the prior art, in particular the so-called eyeliners and mascara, which possess a certain resistance to water and therefore guarantee a long-lasting decorative effect after application. The commercially available eyeliners mainly are in the form of anhydrous gels. However, eyeliners formulated as aqueous gels are also known.

The prior art eyeliners have several drawbacks. In particular, in consideration of their hydrophobicity, the eyeliners are not always easily removable using only water, and often require the use of cleansing compositions for their complete removal.

US 2005/0276771 describes cosmetic compositions, in particular eyeliners and lip cosmetics, able to form, after application, a decorative film adhering to the skin. The film can be removed by peeling, as one would for example with a patch, for example using the fingers or tweezers. Prior to removal, the decorative film must be moistened with water, such as by using a wet swab. The cosmetic compositions described in US 2005/0276771 include at least one emulsion of a hydrophilized polymer, pigments and solid microfibers.

Eyeliners that once applied to the skin can be removed in the form of a film are also known as peel-off eyeliners. This kind of cosmetic products are available commercially, for example, under the brand name Blinc®.

The prior art peel-off eyeliners have several drawbacks. First, their removal is often made difficult by the film tear during peeling. This makes it extremely difficult to remove the product applied with a single peeling action, as is instead highly desirable.

In addition, the decorative stroke traceable on the palpebral rim generally has a relatively low glossiness compared to conventional non-peelable eyeliners.

Finally, the wear of the decorative portion is generally not so long as required or desired for these products (at least 8 hours).

In view of this prior art, the Applicant has set the main objective to overcome the drawbacks outlined above of eyeliners, in particular peel-off eyeliners.

Within this general objective, a first object of the present invention is to provide a cosmetic composition in the form of aqueous gel, in particular usable as an eyeliner which, after application, can be easily removed by peeling.

A second object of the present invention is to provide a cosmetic composition, in particular usable as an eyeliner, which is provided with sufficient water resistance and able to produce a long-lasting decorative effect.

A further object of the present invention is to provide a cosmetic composition, in particular usable as an eyeliner, with which it is possible to make decorative strokes around the eyes with a high precision and glossiness.

The Applicant has now found that the above and other objects that will become apparent hereinafter in the present description can be achieved, according to a first aspect of the present invention, by a cosmetic composition in the form of aqueous gels comprising (percentages by weight referred to the weight of the cosmetic composition):

5%-30% of at least one inorganic pigment;
10%-50% of at least one film-forming agent comprising at least one acrylic copolymer comprising two or more monomers selected from: acrylic acid, methacrylic acid, $C_1$-$C_8$ alkyl acrylate and $C_1$-$C_8$ alkyl methacrylate;
0.05%-3% of at least one thickening agent for aqueous systems;
0.1%-5% of at least one surfactant;
1%-20% of at least one $C_1$-$C_4$ alkanol;
water in an amount equal to the complement to 100%;
said cosmetic composition having a pH in the range 6.5-7.5 and a Brookfield dynamic viscosity (measured at 25° C., speed 50 rpm, rotor S04) in the range 400-5000 cPs.

According to a second aspect thereof, the present invention relates to an applicator device comprising at least one application means and at least one reservoir containing at least one cosmetic composition in the form of an aqueous gel, said cosmetic composition comprising (percentages by weight referred to the weight of the cosmetic composition):

5%-30% of at least one inorganic pigment;
10%-50% of at least one film-forming agent comprising at least one acrylic copolymer comprising two or more monomers selected from: acrylic acid, methacrylic acid, $C_1$-$C_8$ alkyl acrylate and $C_1$-$C_8$ alkyl methacrylate;
0.05%-3% of at least one thickening agent for aqueous systems;
0.1%-5% of at least one surfactant;
1%-20% of at least one $C_1$-$C_4$ alkanol;
water in an amount equal to the complement to 100%;
said cosmetic composition having a pH in the range 6.5-7.5 and a Brookfield dynamic viscosity (measured at 25° C., speed 50 rpm, rotor S04) in the range 400-5000 cPs.

According to a third aspect thereof, the present invention relates to a method for enhancing the aesthetic appearance of the eyes, comprising a step of applying a cosmetic composition in the form of an aqueous gel on at least one palpebral rim to form at least one decorative stroke, said cosmetic composition in the form of an aqueous gel comprising (percentages by weight referred to the weight of the cosmetic composition):

5%-30% of at least one inorganic pigment;
10%-50% of at least one film-forming agent comprising at least one acrylic copolymer comprising two or more monomers selected from: acrylic acid, methacrylic acid, $C_1$-$C_8$ alkyl acrylate and $C_1$-$C_8$ alkyl methacrylate;
0.05%-3% of at least one thickening agent for aqueous systems;
0.1%-5% of at least one surfactant;
1%-20% of at least one $C_1$-$C_4$ alkanol;
water in an amount equal to the complement to 100%;
said cosmetic composition having a pH in the range 6.5-7.5 and a Brookfield dynamic viscosity (measured at 25° C., speed 50 rpm, rotor S04) in the range 400-5000 cPs.

According to a further aspect thereof, the present invention relates to a method for removing a decorative stroke from a palpebral rim of an eye, said decorative stroke having been obtained by applying on said palpebral rim at least one cosmetic composition in the form of an aqueous gel comprising (percentages by weight referred to the weight of the cosmetic composition):

- 5%-30% of at least one inorganic pigment;
- 10%-50% of at least one film-forming agent comprising at least one acrylic copolymer comprising two or more monomers selected from: acrylic acid, methacrylic acid, $C_1$-$C_8$ alkyl acrylate and $C_1$-$C_8$ alkyl methacrylate;
- 0.05%-3% of at least one thickening agent for aqueous systems;
- 0.1%-5% of at least one surfactant;
- 1%-20% of at least one $C_1$-$C_4$ alkanol;
- water in an amount equal to the complement to 100%;

said cosmetic composition having a pH in the range 6.5-7.5 and a Brookfield dynamic viscosity (measured at 25° C., speed 50 rpm, rotor S04) in the range 400-5000 cPs;

said method comprising the steps of:
- wetting said decorative stroke with at least water in order to form a peel-off film;
- removing said peel-off film.

For the purposes of the present description and in the appended claims, the verb "comprise" and all the terms derived therefrom also include the meaning of the verb "consist" and the terms derived therefrom.

Numeric ranges and limits expressed in the present description and in the appended claims also include the numeric value or numeric values mentioned. In addition, all values and sub-ranges of a limit or numeric range are specifically included as if they were explicitly mentioned.

The cosmetic composition according to the present invention is particularly adapted for use as an eyeliner. More specifically, the above cosmetic composition is adapted for use as a peel-off eyeliner.

In fact, the Applicant has unexpectedly found that the cosmetic composition according to the present invention can be applied to the palpebral rim of the eye to enhance the aesthetic appearance thereof, for example by coloring its outline, and can then be removed when desired, quickly, easily and effectively through a peeling action.

The deposition of a dose of the cosmetic composition according to the present invention on the skin is accompanied by the evaporation in a short time of the liquid phase contained therein, resulting in the formation of a thin colored film that remains attached to the skin.

Once dried, the film has a relatively high resistance to the skin and the environment humidity, and thus remains substantially unaltered for several hours (e.g. 10-12 hours). When desired, the film can be easily removed by peeling, after being moistened with at least water.

The action of water, which can be brought into contact with the decorative stroke for example by rubbing a damp sponge thereon causes a reduction in the adhesion of the film to the skin which can thus be removed in its entirety, i.e. without substantially breaking into fragments, with a peeling action.

Without wishing to be bound to any particular theory, it is believed that the highest ease of removal of the cosmetic composition according to the present invention with respect to the peel-off eyeliners known in art is due to the high elasticity of the specific acrylic copolymer used as film-forming agent in the present invention. It has been observed that the best performance in terms of elastic elongation properties of the acrylic copolymer are obtained in aqueous gels with a pH in the range of 6.5-7.5.

The film-forming agent used in the present invention comprises at least one acrylic copolymer comprising two or more monomers selected from: acrylic acid, methacrylic acid, $C_1$-$C_8$ alkyl acrylate and $C_1$-$C_8$ alkyl methacrylate.

Examples of $C_1$-$C_8$ alkyl acrylate radicals are methyl-acrylate, ethyl-acrylate, butyl-acrylate, hexyl-acrylate. Examples of $C_1$-$C_8$ alkyl methacrylate radicals are methyl-methacrylate, ethyl-methacrylate, butyl-methacrylate, hexyl-methacrylate.

In a particularly preferred embodiment, the acrylic polymer is a copolymer comprising at least ethyl-acrylate, methyl-methacrylate and acrylic acid units.

Preferably, the acrylic copolymer has a glass-transition temperature $T_g$ in the range from −25° C. to 0° C., preferably in the range from −20° C. to −5° C.

Preferably, the acrylic copolymer used as film-forming agent is present in the cosmetic composition according to the present invention in an amount in the range of 15%-25% by weight with respect to the total weight of the cosmetic composition.

The acrylic copolymer that can be used as film-forming agent for the purposes of the present invention can be prepared with techniques known to the person skilled in the art and is also available on the market, for example under the brand Daitosol 5000 AD (Daito Kasei Europe).

The product Daitosol 5000 AD is typically formulated as an aqueous emulsion of the acrylic copolymer (50% by weight of copolymer with respect to the total weight of the emulsion). The aqueous emulsion usually contains, in addition to the copolymer and water, also sodium dehydroacetate (antimicrobial) and laureth-21 (decan-1-ol ethoxylate).

In view of the presence of acidic functionalities in the acrylic copolymer used as film-forming agent, the cosmetic compositions according to the present invention may have a pH even below 6.5. In that case, the pH of the cosmetic composition can be changed up to obtain the desired value in the range of 6.5-7.5 by the addition, for example, of an inorganic basifying agent (e.g. ammonia or NaOH) or an organic basifying agent (e.g. 2-amino-2-methyl-1-propanol or 2-amino-2-methyl-1.3-propanediol, L-arginine and the like). Preferably, the basifying agent used is an inorganic basifying agent, more preferably NaOH or KOH.

Preferably, the basifying agent is added to the cosmetic composition according to the present invention in an amount in the range of 0.02%-1.2% by weight with respect to the total weight of the cosmetic composition.

The film-forming agent used in the present invention forms a film having excellent elasticity and adhesion capacity to the skin. The film obtained with the above agent film-forming agent is also transparent and glossy; this film thus allows fixing the pigment to the skin, while obtaining a decorative stroke of intense color and shine.

The cosmetic composition according to the present invention is in the form of aqueous gel. The structure of the aqueous gel originates from the interaction between water and at least one thickening compound for aqueous systems (hereinafter also referred to as "aqueous thickener").

The Brookfield dynamic viscosity of the cosmetic composition according to the present invention is generally in the range of 400-5,000 cPs (centipoises). In the case of eyeliners according to the present invention, the best performance in terms of ease of application and removal can be achieved with compositions having a viscosity in the range of 800-2,000 cPs.

For the purposes of the present description and of the appended claims, unless otherwise indicated, the viscosity values shown are measured with a Brookfield RVDVE instrument at 25° C., speed of 50 rpm (0.83 s$^{-1}$), rotor S04.

Preferably, the thickening agent for aqueous systems is at least one compound selected from: polysaccharides, hydrophilic clays (e.g. hectorite, magnesium silicates and aluminum), crosslinked homopolymers of acrylic acid and mixtures of these compounds.

The polysaccharides that can be used as aqueous thickeners contain, for example, one or more of the following monosaccharide units: galactose, mannose, arabinose, xylose, glucose, fructose or glucuronic acid.

The polysaccharides that can be used for the purposes of the present invention include at least the cellulose derivatives (e.g. hydroxyethyl cellulose, carboxymethyl cellulose, cetyl hydroxyethyl cellulose), vegetable gums of microbial origin (e.g. xanthan gum), the gums derived from plant exudates (e.g. Arabic gum) and starches.

In a particularly preferred embodiment, the aqueous thickener is xanthan gum.

Preferably, the aqueous thickener is present in the cosmetic composition according to the present invention in an amount in the range of 0.1%-1.5% by weight with respect to the total weight of the cosmetic composition.

The cosmetic composition according to the present invention comprises at least one surfactant.

Preferably, said at least one surfactant is an anionic, non-ionic or amphoteric surfactant. The surfactant facilitates the pigment dispersion in the aqueous gel, thus promoting the pigment wetting by water.

Preferably, said at least one surfactant is present in the cosmetic composition according to the present invention in an amount in the range of 0.5%-2% by weight with respect to the total weight of the cosmetic composition.

Examples of anionic surfactants which may be used in the present invention are: polyalkylenglycol ethers of fatty alcohols, taurates, acyl lactylates, stearoyl sodium lactylate, alkyl sulfates, sodium lauryl sulfate, alkyl sulfate polyoxyethylenates, alkyl ether sulfate, monoethanolamine lauryl ether sulfate, alkyl ether carboxylate, monoalkyl phosphate, dialkyl phosphate, mono-(2-hexyldecyl) arginine phosphate, alkyl phosphate ethoxylate, N-acyl sarcosinate, sodium lauryl sarcosinate, sodium myristoyl sarcosinate, N-acylglutamate, sodium lauroyl glutamate, acetyl isethionate, sodium cocoyl isethionate, potassium laurate, potassium myristate, potassium palmitate, potassium stearate, potassium cetyl phosphate and mixtures thereof.

Examples of non-ionic surfactants which may be used in the present invention are: condensation products of alkylene oxides and alkylphenols, such as octylphenol ethoxylate; condensates of ethylene oxide, propylene oxide and ethylenediamine; alkylpolyglucosides; ethers of fatty alcohols and polyols such as for example polyglyceryl-3-hydroxylauryl ether.

Examples of amphoteric surfactants that can be used in the present invention are: betaines and derivatives, sulfobetaines and derivatives, imidazoline derivatives, such as sodium cocoamphodiacetate.

Preferably, the cosmetic composition comprises at least one anionic surfactant. Preferably, the cosmetic composition comprises at least potassium cetyl phosphate (a surfactant consisting of a mixture of phosphoric acid esters and cetyl alcohol salified with potassium ions).

Preferably, the cosmetic composition further comprises at least one $C_2$-$C_{14}$ glycol, preferably a $C_3$-$C_{12}$ glycol. Glycols mainly have a humectant function, and thus promote the preservation of the original features of the cosmetic product over time. Glycols also promote the wettability of the pigment by the aqueous phase and thus contribute to its dispersion in the formulation. Glycols also help to maintain the acrylic copolymer film homogeneous and elastic once this is formed.

Preferably, the cosmetic composition according to the present invention comprises one or more glycols selected from: butylene glycol, pentylene glycol, caprylyl glycol and mixtures thereof.

Preferably, the glycols are present in the cosmetic composition according to the present invention in an overall amount in the range of 0.2%-20% by weight with respect to the total weight of the cosmetic composition, more preferably in the range of 2%-10% by weight.

In order to promote the adhesion of the eyeliner to the skin relatively quickly, the cosmetic composition according to the present invention comprises at least one $C_1$-$C_4$ alkanol. Preferably, said $C_1$-$C_4$ alkanol is selected from ethanol, isopropanol, tert-butanol and mixtures thereof.

Preferably, the $C_1$-$C_4$ alkanol is present in the cosmetic composition according to the present invention in an overall amount in the range of 2%-10% by weight with respect to the total weight of the cosmetic composition.

The cosmetic composition according to the present invention is also characterized by the high amount of pigments that can be used in the formulation. The cosmetic composition according to the present invention comprises one or more pigments in an overall amount in the range of 5-30% by weight with respect to the total weight of the cosmetic composition, preferably in the range of 10-25% by weight.

The pigments that can be used for the purposes of the present invention may be organic or inorganic pigments. Examples of inorganic pigments include: titanium dioxide, zirconium oxide, zinc oxide, cerium oxide, iron oxide, chrome oxide, manganese violet, ultramarine blue, ferric ferrocyanide.

Examples of organic pigments include: carbon black, D&C pigments and lakes, in particular Blue 1 lake.

Preferably, the pigments are selected from: iron oxide, ultramarine blue, carbon black, ferric ferrocyanide, blue 1 lake and mixtures thereof.

The cosmetic composition according to the present invention may also include one or more additives of the type conventionally used in the formulation of cosmetic compositions, particularly in eyeliners. Examples of such additives are: solvents, dispersants, antioxidants, preservatives (e.g. phenoxyethanol, sodium dehydroacetate, EDTA disodium and tetrasodium), fragrances, structuring agents, plasticizers and others.

The additives may be present in the cosmetic composition according to the present invention in an overall amount within the range of 0.1%-10% by weight with respect to the total weight of the cosmetic composition.

The cosmetic composition according to the present invention may be prepared according to the techniques known in the cosmetic industry. The cosmetic compositions according to the present invention may be prepared, for example, through a process that includes the steps of (percentages by weight referred to the weight of the cosmetic composition):

(a) providing at least the following ingredients:
5%-30% of at least one inorganic pigment;
10%-50% of at least one film-forming agent comprising at least one acrylic copolymer comprising two or more monomers selected from: acrylic acid, methacrylic acid, $C_1$-$C_8$ alkyl acrylate and $C_1$-$C_8$ alkyl methacrylate;
0.05%-3% of at least one thickening agent for aqueous systems;
0.1%-5% of at least one surfactant;
1%-20% of at least one $C_1$-$C_4$ alkanol;
water in an amount equal to the complement to 100%, optionally a basifying compound;

(b) mixing the above ingredients to obtain a cosmetic composition having a pH in the range 6.5-7.5 and a Brookfield dynamic viscosity (measured at 25° C., speed 50 rpm, rotor S04) in the range 400-5000 cPs.

The ingredients of the cosmetic composition may be mixed together in any order. Preferably, a mixture containing water, the thickening agent and any glycols is first prepared, stirring the ingredients at room temperature (e.g. 25° C.).

The resulting mixture is then heated up to a temperature of 70-75° C., and then admixed with the optional basifying compound (e.g. aqueous solution of NaOH) in a sufficient amount to bring the pH to the desired value. While keeping the mixture under stirring at a temperature of 70-75° C., the surfactant, the pigment and any additives (e.g. preservatives) are added. The mixture is then brought to a temperature of about 50° C. and admixed with the acrylic copolymer (film-forming agent). The mixture is then cooled to room temperature and admixed with the alkanol, obtaining the final product in the form of aqueous gel.

The cosmetic composition according to the present invention, when used as an eyeliner, can be packaged in an applicator device including at least one application means (e.g. a brush or a textile pad) and at least one tank to contain the cosmetic composition in the form of aqueous gel. Applicator devices that can be used for the purposes of the present invention are known to the person skilled in the art. Applicator devices are described for example in US 2016/0136060, U.S. Pat. Nos. 4,850,727 and 4,974,980.

The following embodiment example is provided purely for illustrative purposes of the present invention and should not be interpreted as limiting the scope of protection defined by the accompanying claims.

EXAMPLE 1—EYELINER ACCORDING TO THE PRESENT INVENTION

A cosmetic composition in the form of aqueous gel was prepared according to the present invention with the following percentage composition by weight:

| iron oxide (black) | 18% |
|---|---|
| acrylic copolymer Daitosol 5000 AD | 20% (*) |
| xanthan gum | 0.3% |
| potassium cetyl phosphate | 1.4% |
| ethyl alcohol | 3.0% |
| butylene glycol | 1.0%; |
| caprylyl glycol | 0.65% |
| pentylen glycol | 3.0% |
| NaOH | 0.08% |
| phenoxyethanol | 0.85% |
| sodium dehydroacetate | 0.2% |
| laureth-21 | 0.12 |
| water | complement to 100%. |

(*) percentage by weight of dry polymer referred to the weight of the cosmetic composition.

The Brookfield dynamic viscosity of the aqueous gel was equal to 1200 cPs (measured at 25° C., speed: 50 rpm, rotor S04) and a pH of 7.2.

The efficacy of the composition as peel-off eyeliner was tested as follows.

A layer of the cosmetic composition was applied at room temperature on the skin of the back of a hand (stroke length: 40 mm; stroke width: 2 mm. 5 minutes were waited to allow the solvent evaporation and the formation of the colored decorative stroke.

The decorative stroke was bright and shiny.

Then, the decorative stroke was wetted with water using a wet swab. The mere contact with water did not give rise to smears of color.

The wet decorative stroke was then slightly scratched with a fingernail, at one end, to pull out a small strip of film from the skin. By grasping it with the fingers on the detached strip, the film was peeled, removing it completely from the skin, without fragmentation.

The invention claimed is:

1. A cosmetic composition in a form of an aqueous gel, comprising (percentages by weight referred to weight of the cosmetic composition):
    greater than or equal to 5% and less than or equal to 30% of at least one organic or inorganic pigment;
    greater than or equal to 10% and less than or equal to 50% of an acrylic copolymer consisting of two or more monomers selected from: ethyl acrylate, methyl methacrylate, or acrylic acid units;
    greater than or equal to 0.05% and less than or equal to 3% of at least one thickening agent for aqueous systems;
    greater than or equal to 0.1% and less than or equal to 5% of potassium cetyl phosphate;
    greater than or equal to 1% and less than or equal to 20% of at least one $C_1$-$C_4$ alkanol; and
    water in an amount equal to the complement to 100%;
    wherein the cosmetic composition has a pH greater than or equal to 6.5 and less than or equal to 7.5, and
    wherein the cosmetic composition has a Brookfield dynamic viscosity (measured at 25° C., speed 50 revolutions per minute (rpm), rotor S04) greater than or equal to 400 centipoise (cPs) and less than or equal to 5,000 cPs.

2. The cosmetic composition of claim 1, wherein the acrylic copolymer has a glass-transition temperature Tg greater than or equal to −25° C. and less than or equal to 0° C.

3. The cosmetic composition of claim 1, wherein the at least one thickening agent for aqueous systems is selected from: polysaccharides, hydrophilic clays, crosslinked homopolymers of acrylic acid, or mixtures thereof.

4. The cosmetic composition of claim 1, wherein the at least one thickening agent for aqueous systems is xanthan gum.

5. The cosmetic composition of claim 1, wherein the at least one $C_1$-$C_4$ alkanol is selected from ethanol, isopropanol, tert-butanol, or mixtures thereof.

6. The cosmetic composition of claim 1, further comprising:
    at least one $C_2$-$C_{14}$ glycol.

7. The cosmetic composition of claim 6, wherein the at least one $C_2$-$C_{14}$ glycol is greater than or equal to 0.2% and less than or equal to 20% by weight with respect to the weight of the cosmetic composition.

8. The cosmetic composition of claim 1, wherein the at least one organic or inorganic pigment is selected from: iron oxide, ultramarine blue, carbon black, ferric ferrocyanide, blue 1 lake, or mixtures thereof.

9. A method for enhancing aesthetic appearance of eyes, comprising applying the cosmetic composition of claim 1 on at least one palpebral rim of an eye to form at least one decorative stroke.

10. The cosmetic composition of claim 1, wherein the Brookfield dynamic viscosity (measured at 25° C., speed 50 rpm, rotor S04) is greater than or equal to 800 cPs and less than or equal to 2,000 cPs.

11. The cosmetic composition of claim 1, wherein the acrylic copolymer has a glass-transition temperature Tg greater than or equal to −20° C. and less than or equal to −5° C.

12. The cosmetic composition of claim 1, wherein the at least one thickening agent for aqueous systems comprises xanthan gum.

13. The cosmetic composition of claim 1, further comprising:
   at least one $C_3$-$C_{12}$ glycol.

14. The cosmetic composition of claim 7, wherein the at least one $C_2$-$C_{14}$ glycol is selected from: butylene glycol, pentylene glycol, caprylyl glycol, or mixtures thereof.

15. The cosmetic composition of claim 1, wherein the at least one organic or inorganic pigment is present in an amount greater than or equal to 10% and less than or equal to 25%.

16. The cosmetic composition of claim 1, wherein the acrylic copolymer is present in an amount greater than or equal to 15% and less than or equal to 25%.

17. The cosmetic composition of claim 1, wherein the at least one thickening agent for aqueous systems is present in an amount greater than or equal to 0.1% and less than or equal to 1.5%.

18. The cosmetic composition of claim 1, wherein the potassium cetyl phosphate is present in an amount greater than or equal to 0.5% and less than or equal to 2%.

19. The cosmetic composition of claim 1, further comprising:
   an organic or inorganic basifying agent.

20. The cosmetic composition of claim 19, wherein the organic or inorganic basifying agent is present in an amount greater than or equal to 0.02% and less than or equal to 1.2%.

* * * * *